United States Patent
Stuart

(10) Patent No.: US 6,226,564 B1
(45) Date of Patent: May 1, 2001

(54) METHOD AND APPARATUS FOR DISPENSING DRUGS TO PREVENT INADVERTENT ADMINISTRATION OF INCORRECT DRUG TO PATIENT

(76) Inventor: John C. Stuart, 7353 W. Vogel, Peoria, AZ (US) 85345

( * ) Notice: Subject to any disclaimer, the term of this patent is extended or adjusted under 35 U.S.C. 154(b) by 0 days.

(21) Appl. No.: 08/742,931

(22) Filed: Nov. 1, 1996

(51) Int. Cl.[7] .................................................. G06F 17/00
(52) U.S. Cl. ....................... 700/231; 700/214; 700/215; 700/235; 700/236; 283/70; 283/81; 283/101; 221/2; 221/4; 221/5
(58) Field of Search ..................... 283/67, 70, 81, 283/101, 105; 221/2, 4, 5; 700/231, 233, 235–236, 237, 238, 239, 240, 241, 242, 243, 244, 245

(56) References Cited

U.S. PATENT DOCUMENTS

| 4,318,477 | * | 3/1982 | Kerpe | 206/534 |
|---|---|---|---|---|
| 4,372,681 | * | 2/1983 | Sallenbach | 356/72 |
| 4,479,573 | * | 10/1984 | Ackley, Sr. et al. | 198/399 |
| 4,548,825 | * | 10/1985 | Voss et al. | 426/383 |
| 4,752,087 | * | 6/1988 | Weisbach | 283/67 |
| 4,895,257 | * | 1/1990 | Winslow | 206/534 |
| 4,951,596 | * | 8/1990 | Wallace, Jr. | 116/321 |
| 5,011,032 | * | 4/1991 | Rollman | 215/230 |
| 5,181,743 | * | 1/1993 | Lloyd | 283/48.1 |
| 5,239,491 | * | 8/1993 | Mucciacciaro | 364/569 |
| 5,413,383 | * | 5/1995 | Laurash et al. | 283/79 |
| 5,435,600 | * | 7/1995 | Griffiths | 283/81 |
| 5,495,961 | * | 3/1996 | Maestre | 221/3 |
| 5,642,906 | * | 7/1997 | Foote et al. | 283/67 |
| 5,713,487 | * | 2/1998 | Coughlin | 221/2 |

* cited by examiner

Primary Examiner—Paul P. Gordon
Assistant Examiner—Ramesh Patel
(74) Attorney, Agent, or Firm—Tod R. Nissle, P.C.

(57) ABSTRACT

A drug dispensation method and apparatus significantly reduces the likelihood that a nurse or other health care personnel will inadvertently administer the wrong drug to a patient. The method and apparatus identify a classification and a characteristic of a drug.

20 Claims, 4 Drawing Sheets

METHOD AND APPARATUS FOR DISPENSING DRUGS TO PREVENT INADVERTENT ADMINISTRATION OF INCORRECT DRUG TO PATIENT

This invention relates to a method and apparatus for dispensing drugs.

More particularly, the invention relates to a drug dispensation method and apparatus which significantly reduces the likelihood that a nurse or other health care personnel will inadvertently administer the wrong drug to a patient.

In the U.S. patients daily die or suffer serious injury due to the inadvertent administration of the wrong medication. Some typical circumstances which result in the administration of the wrong medication are that a nurse misreads the label on a bottle of medicine, that a nurse mistakenly assumes that the bottle she picks up is the same bottle she used the day earlier, that a nurse does not realize that the company selling a particular pharmaceutical has put the pharmaceutical in a new different colored bottle similar to a bottle the nurse is used to opening when using another different pharmaceutical, and, that a nurse has the proper medication but administers it incorrectly.

In addition to the injury suffered by a patient due to the administration of an improper medicament, the well-meaning and dedicated nurse who mistakenly causes the injury inevitably experiences guilt and mental distress, both on a personal basis and as a result of litigation which invariably follows such an incident.

A variety of approaches are available in the prior art which attempt to alert a busy nurse or other medical personnel to the type of medicament being administered to a patient.

Some prior art procedures color code injectable medications. For example, lidocaine can be colored red, epinephrine blue, atropine yellow, calcium green, benadryl orange, etc. Or, heart stimulants can be colored red, heart depressants blue, antihistamines green, blood clotters purple, blood thinners yellow, analgesics orange, etc. See for example, U.S. Pat. No. 5,468,224 to Souryal.

Other prior art apparatus makes the lid of a container a particular color to identify the type of pills in the container. See, for example, U.S. Pat. No. 3,757,994 to Skoetsch.

Still other prior art apparatus colors an intravenous tube holder to correlate to the medicine being administered. For example, if the holder is red, this can indicate that the liquid being administered is critical. If the holder is blue, this might indicate that the liquid being administered is benign. See, for example, U.S. Pat. No. 5,316,246 to Scott et al.

Yet other prior art apparatus uses a colored stick-on tab to correlate an intravenous tube or bottle with a label which is the same color and includes a written description of the fluid being administered and of the site on the patient's body at which the fluid enters the body. See, for example, U.S. Pat. No. 4,795,429 to Feldstein.

Yet still other prior art apparatus colors the lid of a pill container to indicate the number of times each day the medication is to be taken by a patient. See, for example, U.S. Pat. No. 4,883,180 to Humphrey et al.

Other prior art apparatus provides a container with colors which indicate the time a drug is administered and indicate the patient's room number. See, for example, U.S. Pat. No. 3,826,222 to Romick.

Still other prior art apparatus provides medication canisters which carry pressure sensitive, colored patches for identifying the time(s) of day that the medication in the canisters is to be administered to a patient. See, for example, U.S. Pat. No. 5,221,024 to Campbell.

Yet other prior art apparatus provides a medication administration time chart including colored symbols for each medication on the chart. For example, penicillin can be associated with a red star and motrin with a yellow circle. If penicillin needs to be administered to a patient at 1:00 pm, a red star is placed under 1:00 pm on the chart. If motrin needs to be administered to a patient at 2:00 am, a yellow circle is placed under 2:00 am on the chart. See, for example, U.S. Pat. No. 5,261,702 to Mayfield.

Yet still other prior art apparatus provides a tray with compartments for drugs. A particular drug is placed in a compartment along with one or more colored labels. Each particular color of label indicates a time of day that the drug is administered. See, for example, U.S. Pat. No. 3,627,122 to Garbe, Jr.

Other prior art apparatus provides a cassette for dispensing pill packets. The cassette is provided with a color to indicate the time intervals at which the pills are given to a patient. See, for example, U.S. Pat. No. 4,054,343 to Heyland.

Still other prior art apparatus provides a patient tray with colors on the edge of the tray which indicate the time of day particular drugs are administered to a patient. See, for example, U.S. Pat. No. 3,876,268 to Colver.

Yet other prior art apparatus provides a pill container having a colored cap which indicates the frequency with which a pill is administered to a patient. See, for example, U.S. Pat. No. 5,011,032 to Rollman.

The various prior art apparatus noted above is believed to suffer from several disadvantages. First, the prior art apparatus is not accepted because none of the apparatus appears to have been used in any hospital, much less by most hospitals. Second, the prior art apparatus often appears impractical. For example, coloring injectable fluids is difficult because there are only a limited number of colors. The prior art apparently does not disclose any proposal to color pills to identify the drugs in the pills, likely because there are thousands of different types of pills, many of which already are blue, yellow, red, or some other color. Third, the prior art concerned with identifying the time of day that a medicament is administered is not believed pertinent to the problem addressed herein, which is preventing the administration of the incorrect drug. Fourth, identifying a pharmaceutical with a color is ineffective because of the existence of many colored items which are encountered in health care institutions.

Accordingly, it would be highly desirable to provide an improved method and apparatus for enabling nurses and other health care professionals to rapidly confirm without reading a label whether the drug in a container is the drug that the nurse wishes to administer to a patient.

Therefore, it is a principal object of the invention to provide an improved method and apparatus for dispensing drugs to be administered to a patient.

A further object of the invention is to provide an improved method and apparatus for dispensing drugs which does not rely on a single color to correctly dispense a drug.

Another object of the invention is to provide a drug dispensing method and apparatus which can readily be adapted as a standard for use for all health care personnel in a hospital or other health care institution.

Yet a further object of the invention is to provide an improved drug dispensing method and apparatus which provides drug dispensing information in a pre-defined visually recognizable fixed sequence.

Yet still another object of the invention is to provide an improved drug dispensing method and apparatus which is pictorial and does not require the reading and comprehension of alphanumeric characters.

These and other, further and more specific objects and advantages of the invention will be apparent to those skilled in the art from the following detailed description thereof, taken in conjunction with the drawings, in which.

Briefly, in accordance with my invention, I provide improved drug dispensation apparatus including a container; a drug stored in the container; and, an indicia grouping on the container. The indicia grouping includes at least a first indicium indicating a classification for said drug, and at least a second indicium indicating a characteristic of said drug.

In another embodiment of the invention, I provide improved drug dispensation apparatus including a pill including a drug; and, an indicia grouping on the pill. The indicia grouping includes at least a first indicium indicating a classification for the drug, and at least a second indicium indicating a characteristic of the drug.

In a further embodiment of the invention, I provide improved drug dispensation apparatus including a container; a drug stored in the container; a grouping of indicia on the container identifying a classification and at least one characteristic of the drug; and, means indicating a sequence in which the indicia are interpreted.

In still another embodiment of the invention, I provide an improved system for dispensing a drug. The system includes a system for identifying a classification and a characteristic of the drug; a system for correlating the classification of the drug with at least one indicium which indicates the classification of the drug; a system for correlating the characteristic of the drug with at least a second indicium different from the first indicium which indicates the characteristic of the drug; and, a system for producing the indicia on a container in which the drug is dispensed.

In yet another embodiment of the invention, I provide an improved method for dispensing drugs in a hospital. The method includes the steps of providing instruction material indicating the meaning of each of a plurality of indicia, each of the indicia indicating one of the pair comprising a classification of one of the drugs and a characteristic of one of said drugs; providing means for storing the indicia such that each of the drugs can be identified with an indicia grouping including at least one of the indicia indicating the classification of the drug and at least one other of the indicia indicating a characteristic of the drug; dispensing each of the drugs in a container including the indicia grouping identifying the classification and characteristic of the drug. Means can be included on the container for identifying a sequence in which the indicia in the indicia grouping are interpreted.

Figure 1:
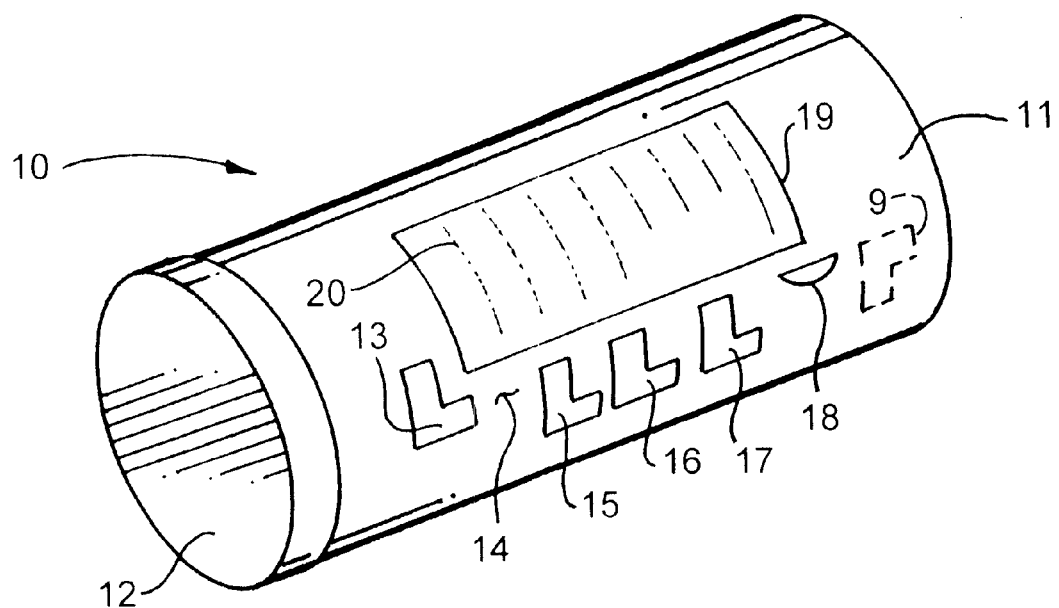
FIG. 1 is a perspective view illustrating a drug dispensing apparatus constructed in accordance with the principles of the invention.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates a drug dispensation apparatus including a container 10 having a hollow cylindrical body 11. One end of body 11 is open and is covered by removable cylindrical cap 12. Label 19 attached to body 11 includes alphanumeric or other characters which typically provide the name of the drug (for example, "Synthroid"), the strength of the drug (for example, "0.15 mg"), the form of the drug (for example, "tab"), the date the prescription was originally filled (for example, "Original: Mar. 21, 1996"), the number of refills (for example, "May Refill 1 Time(s) Until Mar. 21, 1997"), the name of the patient (for example, Debra Williams), the dosage (for example, "Take 1 tablet daily"), the prescription number (for example, "6092723"), the name and address of the pharmacy which filled the prescription, and the name and phone number of the physician authorizing the prescription.

An indicia grouping comprised of colored areas is formed on or in or is attached to body 11. The colored areas comprise areas 13, 15 to 18. While the color of each area 13 to 18 can, as will be described, vary depending on the classification and characteristics of the drug in container 10, it is assumed for sake of example that area 13 is yellow, area 15 is red, area 16 is red, area 17 is black, and area 18 is black; producing the color sequence yellow—red—red—black—black.

A system is provided for determining the sequence in which areas 13 to 18 are interpreted. In FIG. 1, space 14 between areas 13 and 15 is greater than the spaces between each of the pairs 15–16, 16–17, and 17–18. Consequently, the user know that area 13 is read first, then area 15, area 16, area 17, and, lastly, area 18. E.g. areas 13, 15 to 18 are read from left to right. Any other desired system can be utilized to indicate the sequence in which areas 13, 15 to 18 are read. The arabic numeral 1 can be placed in area 13 to indicate that area 13 is read first, followed in ascending order by areas 15 to 18. Or, area 13 can have a gold border which indicates that area 13 is read first, followed by areas 15 to 18 in order. Or, area 13 can be larger than the other remaining areas 15 to 18, indicating that area 13 is read first, followed by areas 15 to 18 in sequential order. The definition of a fixed sequence for reading or interpreting areas 13 to 18 is critical in the practice of the invention. It is not necessary that areas 13 to 18 be read sequentially in ascending order from left to right or from right to left. It might, for example, be possible to read area 13, then area 18, then area 15, area 17, etc. Reading areas 13, 15 to 18 from left to right in strict sequential order (area 13 first, then area 15, 16, 17, and 18) is, however, preferred.

The shape and dimension of each colored area or indicium comprising the indicia grouping on container 10 can vary as desired. Each colored area can be circular, triangular, or take on any other desired shape and dimension. Each colored area can, if desired, have a shape different from that of the other colored areas. One preferred indicia grouping consists of parallel spaced apart color stripes. The colored areas in the indicia grouping on container 10 in FIG. 1 are spaced apart. Colored areas can, if desired, abut, overlap, or be superimposed on one another. Numbers, letters, or other symbols can be utilized as indicia in place of or in conjunction with color, although color is presently preferred. For example, the number "5" can take the place of area 13, the number "3" can take the place of area 15, the number "3" can take the place of area 16, the number "1" can take the place of area 17, and the number "1" can take the place area 18, producing the numerical sequence 5—3—3—1—1.

In FIG. 1, the first indicium (area 13) indicates the classification of the drug in container 10. As used herein, the classification is either the generic name of the drug, the technical scientific name of the drug, or a general class to which the drug belongs. For example, "synthroid" would be a classification of a drug. The more general terminology "respiratory" for another drug which is administered to affect the function of the respiratory tract would also constitute a classification. As used herein, the characteristics of a drug do not include the classification (i.e., the name or class) of the drug but include potency, route of administration or other characteristics of the drug. For example, characteristics which indicate the potency of a drug include the units of measure, the strength, the multiplier, the likelihood of the drug to cause an adverse reaction in a patient's body, the ability of a drug to be intermixed with other drugs prior to adminstration of the drug, and the ability of a drug to be administered to a patient at the same time another drug is administered to a patient or is present in the patient's body. For purposes of interpreting the indicia grouping on the container of FIG. 1, the following classifications are, by way of example and not limitation, assigned with respect to the first indicium (L-shaped area 13) in the indicia grouping: black or the arabic number one indicates an anti-infection drug; brown or the arabic number two indicates a cardiovascular drug; red or the arabic number three indicates a CNS (central nervous system) drug; orange or the arabic number four indicates an ANS (autonomic nervous system) drug; yellow or the arabic number five indicates a respiratory drug; green or the arabic number six indicates a GI tract drug; blue or the arabic number seven indicates a hormonal drug; violet or the arabic number eight indicates hematologic drug; gray or the arabic number nine indicates an anti-neo drug; white or the arabic number ten indicates an immunological drug; gold or the arabic number eleven indicates a nutritional drug; and, silver or the arabic number twelve indicates a miscellaneous drug. Since in FIG. 1, area 13 is yellow, the drug in container 10 is (based on the classifications defined above) a respiratory drug. The drug classification chosen to be represented by a particular color, number or other symbol or indicium can obviously vary as desired.

Area 15 indicates the unit of measure used in determining the potency of the drug in container 10, i.e., area 15 indicates a characteristic of the drug. For purposes of interpreting the indicia grouping on the container 10 in FIG. 1, the following potency units of measure are, by way of example and not limitation, assigned to the second indicium (L-shaped area 15) in the indicia grouping: black or the arabic number one indicates mg/ml as the unit of measure; brown or the arabic number two indicates mcg/ml as the unit of measure; red or the arabic number three indicates grams as the unit of measure; orange or the arabic number four indicates international units as the unit of measure; and, yellow or the arabic number five indicates % as the unit of measure. Since in FIG. 1 area 15 is red, the unit of measure is grams. The unit of measure chosen to be represented by a particular color, number or other symbol or indicium can obviously vary as desired.

Area 16 indicates the route via which the drug is administered to a patient, i.e., area 16 indicates a characteristic of the drug. For purposes of interpreting the indicia grouping on the container 10 in FIG. 1, the following routes of administration are, by way of example and not limitation, assigned to the third indicium (L-shaped area 16) in the indicia grouping: black or the arabic number one indicates I.V. only as the route of administration of the drug; brown or the arabic number two indicates I.M. only as the route of administration of the drug; red or the arabic number three indicates I.V. or I.M. as the route; orange or the arabic number four indicates oral as the route; yellow or the arabic number five indicates rectal as the route; green or the arabic number six indicates optical as the route; and blue or the arabic number seven indicates topical as the route of administration of the drug. Since in FIG. 1 area 16 is red, the route for administering the drug is I.V. or I.M. The route chosen to be represented by a particular color, number or other symbol or indicium can obviously vary as desired.

Area 17 indicates the strength used in determining the potency of the drug, i.e., area 17 identifies a characteristic of the drug. For purposes of interpreting the indicia grouping on the container of FIG. 1, the following classifications are assigned with respect to the fourth indicium (L-shaped area 17) in the indicia grouping: black or the arabic number one indicates a strength of one; brown or the arabic number two indicates a strength of two; red or the arabic number three indicates a strength of two and a half; orange or the arabic number 4 indicates a strength of three; yellow or the arabic number five indicates a strength of four; green or the arabic number six indicates a strength of five; blue or the arabic number seven indicates a strength of six; violet or the arabic number eight indicates a strength of seven; gray or the arabic number nine indicates a strength of eight; and white or the arabic number of ten indicates a strength of nine. Since area 17 is black in FIG. 1, the drug has a strength of one. The strength chosen to be represented by a particular color, number or other symbol or indicium can obviously vary as desired.

Area 18 indicates a multiplier used in determining the potency of the drug, i.e., area 19 indicates a characteristic of the drug. For purposes of interpreting the indicia grouping on the container of FIG. 1, the following classifications are, by way of example and not limitation, assigned with respect to the fifth indicium (area 18) in the indicia grouping: black or the arabic number one indicates a multiplier of one; brown or the arabic number two indicates a multiplier of ten; red or the arabic number three indicates a multiplier of one hundred; and, orange or the arabic number four indicates a multiplier of one thousand. Since area 18 is black in the indicia group of FIG. 1, the drug in container 10 has a multiplier of one. The multiplier chosen to be represented by a particular color, number or other symbol or indicium can obviously vary as desired. The drug in container 10 can comprise a fluid, a pill, a powder, or any other medicament form or material. As would be appreciated by those of skill in the art, drugs ordinarily are administered as a liquid or in the form of a pill.

An additional area 19 can be included to provide information concerning the mixing of a drug, i.e., area 19 can identify an additional characteristic of the drug. For example, if area 19 is black, this can indicate that a drug should not be mixed with other drugs before the drug is administered. If area 19 is brown, this can indicate that the drug should not be administered if there is another drug in a patient's body.

Figure 2:
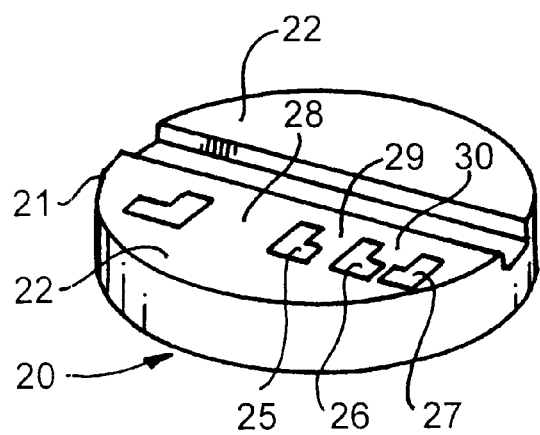
FIG. 2 is a perspective view illustrating an alternate embodiment of the invention.
Figure 3:
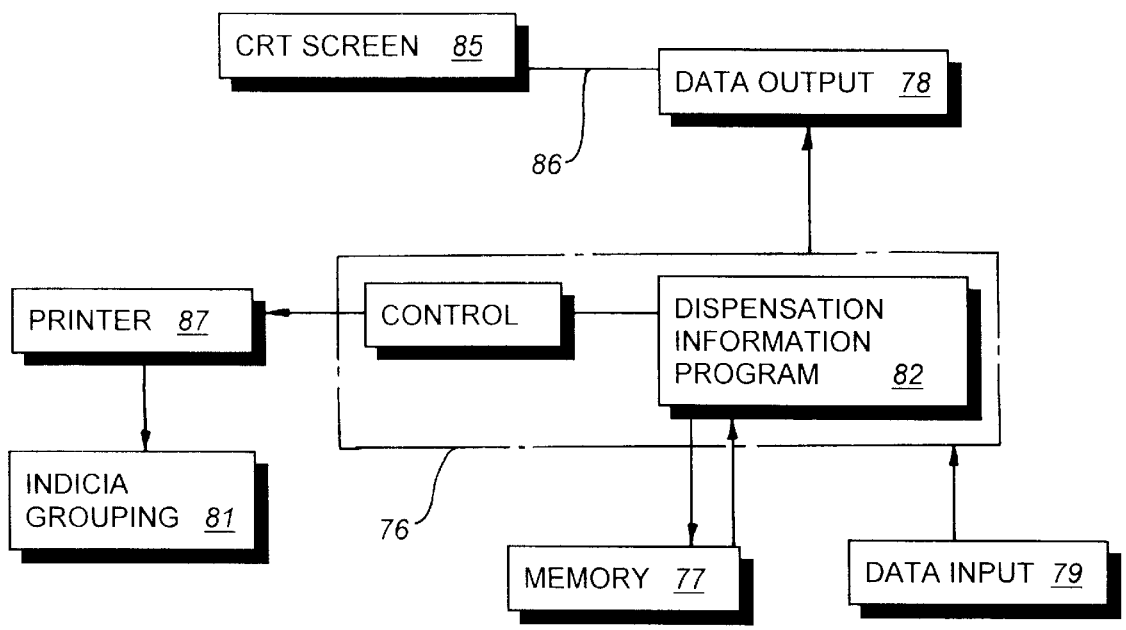
FIG. 3 is a block diagram illustrating another drug dispensing apparatus of the invention.

Another embodiment of the invention is illustrated in FIG. 2 where the drug dispensing apparatus comprises a pill 20. Pill 20 includes at least in part a drug but may, as do most liquids and pills, include a carrier, filler, or other supplemental composition or material. An indicia grouping is formed on pill 20. The indicia grouping includes colored areas, namely spaced apart areas 21, 25, 26, 27. The shape, dimension, and configuration of the indicia in the indicia group can vary as desired in accordance with the foregoing discussion. The indicia grouping on pill 20 is, for the sake of simplicity, interpreted using the same procedure that was used above to interpret the indicia grouping 13, 15 to 18 on container 10. Area 21 is blue, area 25 is orange, area 26 is orange, and area 27 is black.

Since in FIG. 2 the space 28 between area 21 and area 25 is greater than the spaces 29 and 30 between adjacent areas 25–26 and 26–27, respectively, area 21 is interpreted first, followed by areas 25, 26, 27. Since area 21 is blue, the medication in pill 20 is hormonal. Since area 25 is orange, the units of measure are international units. Since area 26 is orange, the route of administration of the drug is oral. Since area 27 is black, the strength of the drug is one.

Another embodiment of the invention is depicted in FIGS. 3 to 6. The block diagram of FIG. 1 illustrates a system for dispensing a drug and includes a computer including a controller 76 and a memory 77. Data input 79 (a keyboard, punched card reader, paper tape reader, optical scanner, etc.) and data output 78 (a printer, visual display etc.) are provided. Data output 78 can display 86 information on a CRT screen 85.

The computer can be a digital computer, analog computer, hybrid computer, or other programmable apparatus. In practice, the very large majority of computers comprise digital computers.

The memory 77 can be any suitable prior art memory unit such as are commonly used in digital or other computers. For example, electromagnetic memories such as magnetic, optical, solid state, etc. or mechanical memories such as paper tape.

Data input 10 provides 83 data to class, potency, and route generation 82A and to indicia grouping generation 82B, as well as providing 80 information to class, potency, and route information 77A and indicia grouping information 77B. Data can be input into memory 77 well prior to the dispensing of a drug and/or at the time the drug is being dispensed. By way of example, and not limitation, it is anticipated that the classification of a large variety of drugs (whether they are anti-infection, respiratory, CNS, ANS, etc.) will be stored in memory 77 such that when a prescription is being filled or drugs are being dispensed by a pharmacist or machine into a container 10, the controller 76 will automatically instantly classify the drug as soon as the pharmacist or machine types or enters the trade name or generic name of the drug. Memory 77 may also include stored information concerning the route of administration of a drug. On the other hand, the pharmacist or machine likely, but not necessarily, will enter potency information such as the unit of measure, strength, and multiplier at the time the drug is being dispensed. Once the classification, potency, and route information 77A are entered in memory 77A, the class, potency, and route generation sub-routine defines the class, potency, and route for the drug, after which the indicia grouping generation sub-routine 82B utilizes the indicia grouping information 77B to define an indicia grouping for the drug.

The indicia grouping information 77B correlates the drug class and characteristics (potency, route factors, or other factors) each with a particular indicium. For example, based on the criteria discussed above in evaluating the indicia groupings illustrated in FIGS. 1 and 2, if the classification of the drug being dispensed is respiratory, this classification is correlated with the color yellow; if the unit of measure is mg/ml, the indicia grouping generation sub-routine 82B correlates this unit of measure with the color black; if the administration route is oral, then routine 82B correlates this route with the color orange; and so on. In other words, the color or other indicia to be associated with each particular drug classification and characteristic is normally predefined and stored in memory 77, although such definition and storage can, if desired, take place at the time a drug is being dispensed.

Figure 4:
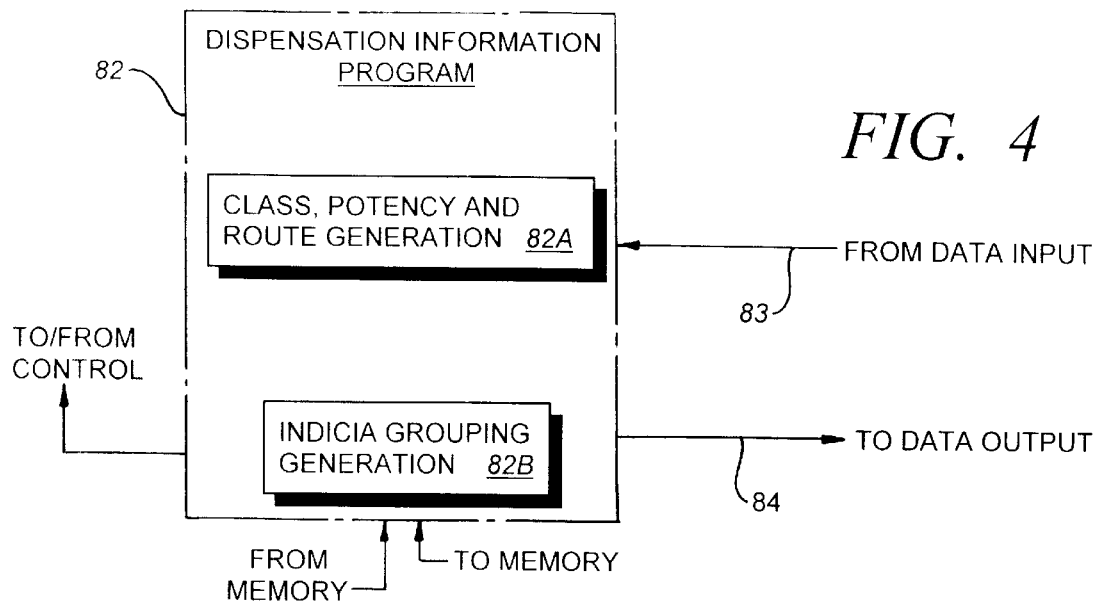
FIG. 4 is a block diagram illustrating the dispensation information program of FIG. 3.
Figure 5:
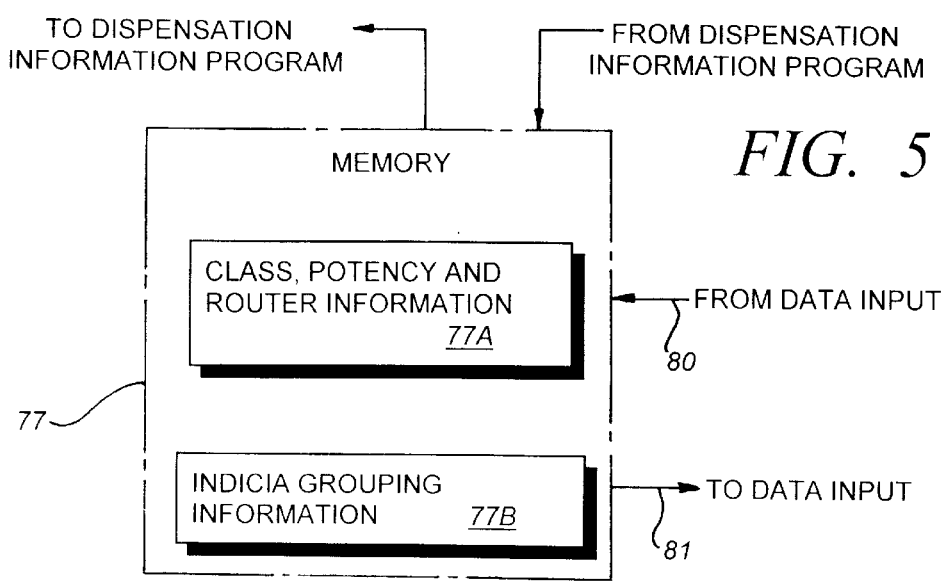
FIG. 5 is a block diagram illustrating the memory of the drug dispensing apparatus of FIG. 3; and, FIG. 6 is a block flow diagram illustrating a typical logic function utilized by the dispensation information program of FIG. 3.

As shown in FIG. 4, the dispensation information program 82 in the controller 76 performs the dual function of class, potency, and route generation 82A and indicia grouping generation 82B.

Class, potency, and route information 77A is utilized by controller 76 during class, potency, and route generation 82A. Indicia grouping information 77B is utilized by the controller 76 during indicia grouping generation 82B. After an indicia grouping is prepared for a drug being dispensed, the controller 26 transmits the grouping to printer 87. Printer produces the indicia grouping 81, typically by imprinting the indicia grouping on a label, a container, or a pill.

Figure 6:
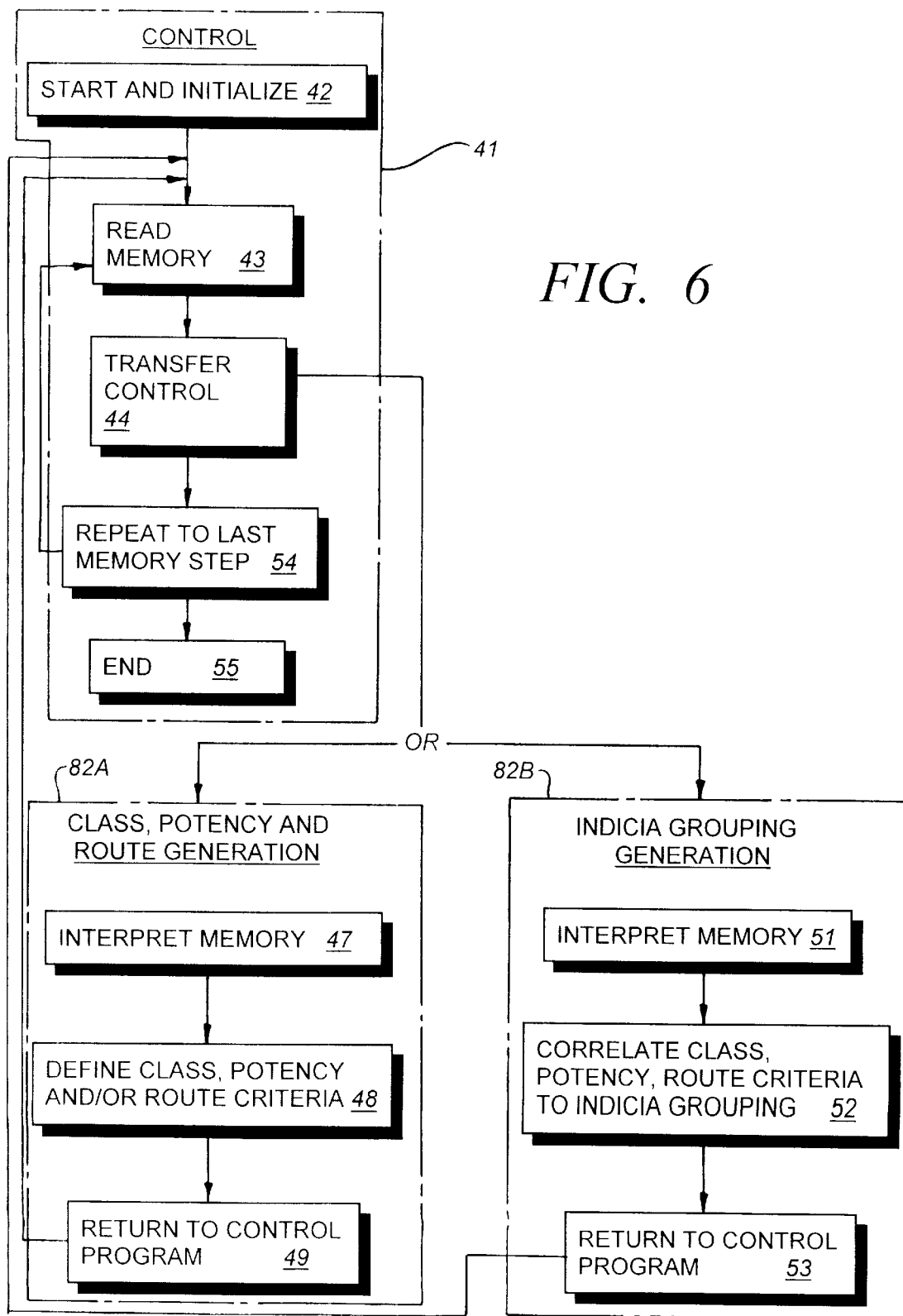

FIG. 6 is a block flow diagram which illustrates a typical program or logic function which is executed by the controller 76. The basic control program 41 consists of commands to "start and initialize" 42, "read memory" 43 and "transfer control" 44 to either the class, potency and route generation sub-routine 82A or the indicia grouping generation sub-routine 82B.

The class, potency, and route sub-routine 82A consists of commands to "interpret memory" 47, "define class, potency, and/or route criteria" 48, and "return to control program" 49. The indicia grouping generation sub-routine 82B consists of commands to "interpret memory" 51, "correlate class, potency, and/or route criteria to indicia grouping" 52, followed by "return to control program" 53. The control program 41 and class, potency and route generation 82A and indicia grouping generation subroutines are repeated as indicated by the "repeat to last memory step" 54 of the control program 41 followed by an "end" program step 55 which completes the execution of the program.

Once the indicia which are used to formulate the indicia groupings for a variety of different drugs are selected, a printed manual or other instruction material can be prepared which identifies the indicia, which explains which drug classification or characteristic correlates with a particular indicium, and which explains how the indicia are sequentially read to interpret an indicia grouping. If the indicia are utilized consistently on all or most pharmaceutical containers or pharmaceuticals dispensed in a hospital, the health care professionals in the hospital soon learn to discern at a glance the classification, potency, route of administration (or other selected characteristics) of a dispensed drug. The ability to so correlate the classification and at least one characteristic of a drug significantly reduces the likelihood that the wrong drug will be administered to a patient.

In use, the classification and desired characteristics are determined for a drug being dispensed. The classification and desired characteristics are each correlated with a pre-defined indicium. The indicium are assembled into an indicia grouping. The indicia grouping could, for example, comprise a series of spaced apart colored stripes or bands. The indicia grouping is imprinted, drawn, or otherwise formed on a container for the drug, on a pill carrying the drug, or on other drug dispensation apparatus. Each of the indicium in the indicia grouping is subsequently read or interpreted in a selected sequence to identify the classification and characteristics of the dispensed drug.

Having described my invention and the presently preferred embodiments thereof in a manner understandable to those of skill in the art, I claim:

1. Drug dispensation apparatus including
   (a) a container;
   (b) a drug stored in said container;

(c) a plurality of classification indicia each different from the other and comprising a symbol which is defined to
  (i) correspond to, and
  (ii) be interpreted by eye to identify a different drug classification;
(d) a plurality of characteristic indicia each different from the other and comprising a symbol which is defined to
  (i) correspond to, and
  (ii) be interpreted by eye to identify a different drug characteristic; and
(e) an indicia grouping on said container and including
  (i) at least a first one of said classification indicia identifying a classification for said drug, and
  (ii) at least a first one of said characteristic indicia adjacent said first classification indicia and identifying a first characteristic of said drug, said indicia in said indicia grouping being in a selected sequence which
  (iii) is interpreted by eye, and
  (iv) indicates which of said indicia identifies a classification of said drug and which of said indicia identifies a characteristic of said drug.

2. The drug dispensation apparatus of claim 1 wherein said indicia grouping includes a second one of said characteristic indicia adjacent said first one of said characteristic indicia and identifying a second characteristic of said drug different from said first characteristic.

3. The drug dispensation apparatus of claim 1 wherein said indicia each comprise a colored area.

4. The drug dispensation apparatus of claim 3 wherein each classification indicia has a color different from each of the other remaining classification indicia.

5. The drug dispensation apparatus of claim 4 wherein each characteristic indicia has a color different from each of the other remaining characteristic indicia.

6. The drug dispensation apparatus of claim 5 where each of said indicia is a stripe.

7. The drug dispensation apparatus of claim 1 wherein
(a) said drug classifications are selected from the group consisting of
  (i) the generic name of at least one drug,
  (ii) the technical scientific name of at least one drug, and
  (iii) at least one drug class; and,
(b) said characteristic is selected from the group consisting of
  (i) the potency of at least one drug, and
  (ii) the route of administration of at least one drug.

8. The drug dispensation apparatus of claim 1 wherein each of said symbols is unitary.

9. The drug dispensation apparatus of claim 8 wherein said indicia grouping includes a second one of said characteristic indicia adjacent said first one of said characteristic indicia and identifying a second characteristic of said drug different from said first characteristic.

10. The drug dispensation apparatus of claim 9 wherein at least one of said symbols is circular.

11. The drug dispensation apparatus of claim 9 wherein at least one of said symbols is triangular.

12. The drug dispensation apparatus of claim 9 wherein each of said symbols is a stripe.

13. Drug dispensation apparatus including
(a) a pill including a drug; and
(b) an indicia grouping on said pill and including
  (i) at least a first indicium consisting of a symbol representing a classification for said drug, and
  (ii) at least a second indicium consisting of a symbol representing a characteristic of said drug,
said indicia in said indicia grouping being in a selected sequence which is interpreted by eye and indicates which of said indicia identifies a classification of said drug and which of said indicia identifies a characteristic of said drug.

14. The drug dispensation apparatus of claim 13 wherein
(a) said classification is selected from the group consisting of
  (i) the generic name of at least one drug,
  (ii) the technical scientific name of at least one drug,
  (iii) at least one general drug class; and,
(b) said characteristic is selected from the group consisting of
  (i) potency of at least one drug, and
  (ii) route of administration of at least one drug.

15. The drug dispensation apparatus of claim 14 wherein said indicia each comprise a unitary symbol.

16. The drug dispensation apparatus of claim 15 wherein said symbols are each non-alphanumeric.

17. Drug dispensation apparatus including
(a) a container;
(b) a drug stored in said container;
(c) a grouping of indicia on said container including a classification indicium which is defined to correspond to and be interpreted by eye to identify a classification and a characteristic indicium which is defined to correspond to and be interpreted by eye to identify a characteristic of said drug; and,
(d) means indicating
  (i) a sequence in which said indicia are interpreted by eye,
  (ii) the classification corresponding to said classification indicium, and
  (iii) the characteristic corresponding to said characteristic indicium.

18. A system for dispensing a drug including
(a) a plurality of classification indicia each different from the other and comprising a symbol which is defined to correspond to and be interpreted by eye to identify a different drug classification;
(b) a plurality of characteristic indicia each different from the other and comprising a symbol which is defined to correspond to and be interpreted by eye to identify a different drug characteristic;
(c) means for identifying each of a plurality of drugs a reference classification and at least one reference characteristic of the drug, said reference classification and said reference characteristic accurately defining a classification and characteristic, respectively, of the drug;
(d) means for correlating said reference classification of the drug with one of said classification indicia which corresponds to and is interpreted by eye to identify said reference classification;
(e) means for correlating said characteristic of the drug with one of said characteristic indicia which is corresponds to and is interpreted by eye to identify said one of said characteristics;
(f) a plurality of containers, each of said drugs being dispensed in a different one of said containers; and
(g) means for producing said one of said characteristic indicia and said one of said classification indicia for each of said drugs in an identical selected sequence on said containers in which said drugs are dispensed.

19. A method of dispensing drugs in a hospital including
(a) providing instruction material indicating the meaning of each of a plurality of indicium, each of said indicium comprising a symbol interpreted by eye and indicating one of the pair including
  (i) a classification of one of said drugs, and
  (ii) a characteristic of one of said drugs;
(b) providing means for storing said indicia such that each of said drugs can be identified with an indicia grouping including at least one of said indicium indicating a classification of said drug and including at least one other of said indicium indicating a characteristic of said drug;
(c) providing a plurality of containers, each of said drugs being dispensed in a different one of said containers;
(d) dispensing each of said drugs in one of said containers, each of said containers including said indicia grouping interpreted by eye to identify said classification and characteristic of said drug;
(e) interpreting by eye said indicia grouping on a selected one of said containers and dispensing drugs from said selected one of said containers.

20. The method of claim 19 including means for identifying which of said indicia in said indicia grouping indicates said classification of said drug and which of said indicia in said indicia grouping indicate said characteristic of said drug.

* * * * *